United States Patent [19]

Perregaard

[11] 4,353,910
[45] Oct. 12, 1982

[54] DERIVATIVES OF 4,5,6,7-TETRAHYDROISOXAZOLO [5,4-C] PYRIDINE-3-ONE, PHARMACEUTICAL COMPOSITIONS AND METHODS OF TREATMENT

[75] Inventor: Jens K. Perregaard, Oelstykke, Denmark

[73] Assignee: Kefalas A/S, Copenhagen-Valby, Denmark

[21] Appl. No.: 325,292

[22] Filed: Nov. 27, 1981

[51] Int. Cl.³ .................. C07D 498/04; A61K 31/44
[52] U.S. Cl. .................................. 424/256; 546/116
[58] Field of Search ..................... 546/116; 424/256

[56] References Cited

PUBLICATIONS

Krogsgaard-Larsen et al., *Chem. Abstracts*, vol. 88 (1978), No. 32321p.

*Primary Examiner*—Robert W. Ramsuer
*Attorney, Agent, or Firm*—Gordon W. Hueschen

[57] ABSTRACT

Carbamoyl derivatives of 4,5,6,7-Tetrahydroisoxazolo[5,4-c] Pyridine-3-one, and method of preparation, pharmaceutical compositions thereof, and methods of treatment of GABA-system malfunctions therewith, are all disclosed.

8 Claims, No Drawings

DERIVATIVES OF 4,5,6,7-TETRAHYDROISOXAZOLO [5,4-C] PYRIDINE-3-ONE, PHARMACEUTICAL COMPOSITIONS AND METHODS OF TREATMENT

The present invention relates to hitherto unknown compounds of the formula

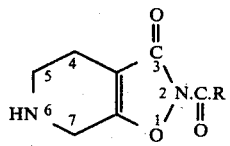

wherein R is an alkyl group, branched or unbranched, having from one to seventeen carbon atoms inclusive, a phenyl group optionally substituted with one or two groups selected from lower alkyl, lower alkyloxy and halogen, a phenylalkyl group, lower alkyloxy group or a —$NHR^1$ group, wherein $R^1$ is hydrogen, lower alkyl, phenyl or cyclohexyl, as well as pharmaceutically acceptable acid addition salts thereof, which are shown to have gamma-aminobutyric acid (GABA) related activity and are indicated for use in treating GABAsystem malfunction-related diseases such as epilepsy, parkinsonisme, schizophrenia, Huntington's chorea, diseases involving malfunction of the pituitary hormones, and cerebral arterioschlerosis.

They moreover show strong analgesic and myotonolytic effects.

The compound 4,5,6,7-tetrahydroisoxazolo[5,4-c]pyridine-3-ol (shortly called THIP in the following) has recently been described as having GABA-related activity, for example in European Patent Application No. 78 100 191.2. It is, however, relatively shortacting and has also some side effects.

In accordance with the present invention it has now surprisingly been found that compounds of Formula I as well as their pharmaceutically acceptable acid addition salts show GABA-related activity at the same level as does the compound THIP, and some of the novel compounds of the invention also show a prolonged effect compared with THIP. They moreover show pronounced analgesic and myotonolytic effects.

The invention further relates to novel pharmaceutical compositions containing as an active ingredient a compound of Formula I or a pharmaceutically acceptable acid addition salt thereof.

The present invention also comprises a method for the preparation of compounds of Formula I, and methods for the treatment of GABA system malfunction-related diseases, a method for alleviating pain of varying aetiology and a method of treating myotonic conditions (e.g. in inducing muscle relaxation or in treating muscle spasm or muscular spasticity.

The terms "lower alkyl" and "lower alkyloxy" groups comprise such groups having from one to six carbon atoms inclusive.

As examples of pharmaceutically acceptable salts of the compounds of the Formula I may be mentioned salts with inorganic acids, e.g. hydrochlorides, hydrobromides, nitrates, sulfates, phosphates and the like, or with organic acids such as acetates, propionates, glycolates, malonates, maleates, succinates, fumarates, tartrates, citrates, oxalates, benzoates, pamoates, methane sulfonates, ethane sulfonates, benzen sulfonates, toluene sulfonates and the like, which salts may be prepared by procedures known per se, e.g. by adding the acid in question to the base, preferably in a solvent.

According to the method of the invention a compound of the formula

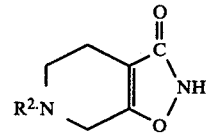

wherein $R^2$ is an amino-protecting group readily removable, is acylated with a reactive derivative of an acid of the formula R.COOH, wherein R is as defined above, at reflux temperature, whereupon the protecting group $R^2$ is split off and the compound of Formula I isolated as the free base or a pharmaceutically acceptable acid addition salt thereof.

When R is a —$NHR^1$ group it has proved especially advantageous to use as a reactive derivative an isocyanate of the formula $R^1$—N=C=O.

As protecting groups $R^2$ are preferably used groups which may subsequently be split off quite easily such as alkyloxycarbonyl groups. Preferably tertiary butyloxycarbonyl-substitution was used according to the method described by Tarbell et al, Proc.Nat.Acad.Sci. 69 (3), p.730, 1972.

The N-acylation according to the method of the invention is preferably carried out in conventional manner in an organic solvent at reflux temperature.

Some of the starting materials of Formula II are conveniently prepared by reaction of 4,5,6,7-tetrahydroisoxazolo[5,4-c]-pyridine-3-ol (in the following called THIP for short) with a dialkyldicarbonate, preferably ditertiary butyl dicarbonate.

After the acylation according to the method of the invention the protecting group $R^2$ may be removed under mild conditions such as controlled hydrolysis. When $R^2$ is a tertiary butyloxy carbonyl group it may conveniently be removed by reaction with anhydrous trifluoroacetic acid at about 0° C. Centigrade.

The method of the invention is illustrated by the following working examples, which may not be construed as limiting.

EXAMPLE 1

3-Hydroxy-6-(t-butyloxycarbonyl)-4,5,6,7-tetrahydroisoxazolo[5,4-c]pyridine (t-BOC THIP)

THIP,HBr (11.1 g) was suspended in 50 ml of dioxane and 25 ml of water. By addition of NaOH (4.0 g) in 25 ml of water under ice cooling a clear solution was obtained. Di-t-butyl dicarbonate (11.0 g) was added and the temperature was raised to 25° C. The mixture was vigorously stirred for another 1.5 hour. Ethyl acetate (300 ml) and water (100 ml) were added and the pH of the aqueous solution was adjusted to ~3.0 with a $KHSO_4$ solution. The ethyl acetate phase was separated and washed with 2×25 ml of water, dried over anhydrous $MgSO_4$ and the solvent evaporated leaving 11.8 g (98%) of product. M.P. 134°–136° C., IR (KBr): $\nu_{OH}$ 2400–3200 (broad, complex bands), $\nu_{C=O}$1690 cm$^{-1}$.

EXAMPLE 2

2-Benzoyl-4,5,6,7-tetrahydroisoxazolo[5,4-c]pyridine-3-one, and its oxalate t-BOC THIP (2.4 g) was refluxed with benzoic acid anhydride (2.5 g) in 40 ml of $CHCl_3$ for 13 hours. The organic solution was washed with ice cooled 0.1 M $K_2CO_3$-solution (2×25 ml), dried over anhydrous $MgSO_4$ and $CHCl_3$ evaporated. The remaining oil was dissolved in 20 ml of a 1:1 mixture of ether and n-hexane. After stirring and cooling for a while, 2-benzoyl-6-(t-butyloxycarbonyl)-4,5,6,7-tetrahydroisoxazolo[5,4-c]pyridine-3-one precipitated. Yield: 1.3 g (38%). M.P. 126°–128° C.

This product was added to 10 ml of ice cooled anhydrous trifluoroacetic acid. The mixture was stirred until the $CO_2$-evolution had stopped. Excess trifluoroacetic acid was evaporated and the resulting oil dissolved in a few milliliters of dry acetone. Anhydrous oxalic acid (2 grams) in 10 ml of dry acetone was added. Under stirring and cooling the oxalate of 2-benzoyl-4,5,6,7-tetrahydroisoxazolo[5,4-c]-3-one precipitated. Yield: 89%. M.P. 210°–213° C. (dec.) (Found: C 53.22; H 4.45; N 8.08; $C_{15}H_{14}N_2O_7$ requires: C 53.89; H 4.23; N 8.38%).

EXAMPLE 3

2-Acetyl-4,5,6,7-tetrahydroisoxazolo[5,4-c]-pyridine-3-one, and its oxalate t-BOC THIP (7.2 g) was refluxed with acetic acid anhydride (5.0 g) in 50 ml of $CHCl_3$ for 2 hours. 2-Acetyl-6-(t-butyloxycarbonyl)-4,5,6,7-tetrahydroisoxazolo[5,4-c]pyridine-3-one was isolated as an oil in 6.4 g (76%) yield by column chromatography (Silicagel 60 "Merck") (eluted with ether/$CH_2Cl_2$ (1:3)). The t-BOC group was split off as above, yielding 73% of the oxalate. M.P. 177°–178° C. (dec.) (Found: C 44.32; H 4.70; N (10.58); $C_{10}H_{12}N_2O_7$ requires C 44.12; H 4.45; N 10.29%).

EXAMPLE 4

2-Isobutyryl-4,5,6,7-tetrahydroisoxazolo[5,4-c]-pyridine-3-one, and its oxalate

The intermediate, 2-isobutyryl-6-(t-butyloxycarbonyl)-4,5,6,7-tetrahydroisoxazolo[5,4-c]pyridine-3-one was prepared and isolated as described in Example 3 in 82% yield. M.P. 118°–119° C. The t-BOC group was split off as above, yielding 94% of the oxalate. M.P. 174°–176° C. (dec.) (Found: C 47.72; H 5.50; N 9.45; $C_{12}H_{16}N_2O_7$ requires C 47.99; H 5.38; N 9.33%).

EXAMPLE 5

2-Carbamoyl-4,5,6,7-tetrahydroisoxazolo[5,4-c]-pyridine-3-one, and its oxalate

To a suspension of potassium cyanate (3.2 g) in 50 ml of $CH_2Cl_2$ was added a solution of trifluoroacetic acid (4.0 g) in 50 ml of $CH_2Cl_2$ at 0° C. t-BOC THIP (4.8 g) dissolved in 100 ml of $CH_2Cl_2$ was slowly added under cooling. The mixture was further stirred at room temperature for 0.5 hour. The whole reaction mixture was submitted to column chromatography without evaporating $CH_2Cl_2$. 2-Carbamoyl-6-(t-butyloxycarbonyl)-4,5,6,7-tetrahydroisoxazolo[5,4-c]pyridine-3-one was eluted with 10% methanol in ether. Yield: 4.6 g (81%). M.P. 129°–131° C. The t-BOC group was split off as above, yielding 87% of the oxalate. M.P. 209°–210° C. (dec.) (Found: C 39.48; H 4.24; N 15.31; $C_9H_{11}N_3O_7$ requires: C 39.56; H 4.07; N 15.38%).

EXAMPLE 6

2-(N-methylcarbamoyl)-4,5,6,7-tetrahydroisoxazolo[5,4-c]pyridine-3-one, and its oxalate t-BOC THIP (4.8 g) was refluxed with methylisocyanate (3.0 g) in 50 ml of $CH_2Cl_2$ for 1.5 hour. The solvent was evaporated. The remaining solid was stirred with cold isopropylether yielding 5.4 g (91%) of 2-(N-methylcarbamoyl)-6-(t-butyloxycarbonyl)-4,5,6,7-tetrahydroisoxazolo[5,4-c]pyridine-3-one. M.P. 134°–135° C. The t-BOC group was split off as above yielding 90% of the oxalate. M.P. 168°–169° C. (dec.) (Found: C 41.60; H 4.74; N 14.43; $C_{10}H_{13}N_3O_7$ requires: C 41.81; H 4.57; N 14.63%).

EXAMPLE 7

2-(N-cyclohexylcarbamoyl)-4,5,6,7-tetrahydroisoxazolo[5,4-c]pyridine-3-one, and its oxalate t-BOC THIP (3.6 g) was refluxed with cyclohexylisocyanate (1.9 g) in 50 ml of $CH_2Cl_2$ for 2 hours. Most of the $CH_2Cl_2$ was evaporated and by addition of n-hexane 2-(N-cyclohexylcarbamoyl)-6-(t-butyloxycarbonyl)-4,5,6,7-tetrahydroisoxazolo[5,4-c]pyridine-3-one precipitated. Yield: 4.8 g (88%). M.P. 92°–94° C. The t-BOC group was split off as above, yielding 87% of the oxalate. M.P. 204°–205° C. (dec.) (Found: C 50.53; H 6.17; N 11.45; $C_{15}H_{21}N_3O_7$ requires: C 50.69; H 5.97; N 11.83%).

EXAMPLE 8

2-(N-phenylcarbamoyl)-4,5,6,7-tetrahydroisoxazolo[5,4-c]pyridine-3-one, and its oxalate t-BOC THIP (4.8 g), triethylamine (2.1 g) and phenylisocyanate (2.5 g) were refluxed in 50 ml of dry tetrahydrofuran for 1.5 hour. Volatile material was evaporated and the remaining oil was dissolved in 100 ml of ether. 2-(N-phenylcarbamoyl)-6-(t-butyloxycarbonyl)-4,5,6,7-tetrahydroisoxazolo[5,4-c]pyridine-3-one precipitated from the solution. Yield: 4.9 g (68%). M.P. 152°–154° C.

The t-BOC group was split off as above yielding 90% of the oxalate. M.P. 214°–218° C. (dec.) (Found: C 52.02; H 4.40; N 12.01; $C_{15}H_{15}N_3O_7$ requires: C 51.57; H 4.34; N 12.03%).

The compounds of Formula I were tested according to standard reliable test methods, which are described in the following

Isoniazide antagonism

Mice, male, 20–25 g
Isoniazide 300 mg/kg s.c.
Macrolon cages type II

Dosage and procedure

The test compound is injected i.p. in the doses 0, ¼, ⅛ and 1/32 of the determined "i.v. LD50". In case of insoluble substances the doses 0, ¼, 1/16 and 1/64 of the determined "i.p. LD50" are used.

Five mice are used for each dose level.

Immediately after administration of test substance, isoniazide 300 mg/kg is injected s.c. This dose of isoniazide induces intermittent tonic clonic seizures within 60 minutes.

The calculations are performed as an "on line procedure" on the EDP-terminal. The results are recorded as % increase in time until convulsions occur and in addition the least dose (MED) which shows significant effect (minimal effective dose, calculated by means of Van der Waerden-test). $ED_{50}$ is determined as the dose in mg/kg which increases the time 50%.

Mouse grid shock

Mice, male, 20–23 g.

The mouse grid consists of a perspex cage with wire grid bottom and a perspex lid, on which is placed a microphone sensitive to the frequency of a mouse-squeak. A stimulator with motordriven potentiometer applies a sequence of square wave impulses of continuously increasing milliamperage to the grid. Frequency of impulses 20 cycles/sec., duration 5 msec. Milliamperage is recorded on a digital amperemeter connected to the stimulator. Activation of the microphone by a mouse-squeak cuts off the current and the final milliamperage appear on the meter.

Dosage and procedure

The test substance is given i.p. in the doses ½, ¼ and ⅛ of the determined "i.v. LD50". For insoluble substances the doses ¼, ⅛ and 1/16 of the "i.p. LD50" are used. Five mice are used for each dose level. Each mouse serves as its own control.

Prior to the administration of test substance the animals are placed on the grid one at a time and the pain threshold is determined by increasing the current intensity until the mouse squeaks. The pain threshold may be read on the milliamperemeter.

Fifteen minutes and 30 minutes after administration of test substance the mice are tested again and the pain thresholds recorded. Furthermore the test substance may be tested after oral administration in the doses 1/1, ½ and ¼ of "the i.v. LD50", and the pain threshold is determined before and 30 min. after the administration. Insoluble test substances are tested orally in the doses of ½, ¼ and 1/8 of the "i.p. LD50".

Analgesic effect is present when the pain threshold is increased over the pre-dosing value (control value). The results are stated as % increase in pain threshold calculated on the basis of the control value. The registration can also be done as an on-line procedure. In this case the punching instruction and punching cards will be provided automatically and the results will be registered as a minimal effective dose (MED) determined after van der Waerden's X-test.

$^3$H-GABA binding to rat brain membranes

Rats 125–200 g
0.32 M sucrose (made fresh every day)
10% Triton X-100
0.05 N Tris-citrate buffer (pH ~6.8)
 6.05 g Trisma ® (base)
 3.502 citric acid, $H_2O$
 to 1 liter of water
$^3$H-GABA = aminobutyric acid, γ-2,3-$^3$H(N) approx. 35 Ci/mmol, from New England Nuclear (diluted daily to 1 μM in water)

Procedure

A. Preparation of membranes

Rats are killed by a blow to their head, exsanguinated and their brains removed and cooled in icecold saline. After rinsing and weighing two brains are pooled and homogenized in 40 ml of icecold 0.32 M sucrose using a motor-driven homogenizer with teflon pestle (6 strokes up and down, slow speed rotation).

The samples are centrifuged for 10 min. at 900 g, and thereafter the supernatants are centrifuged for 20 min. at 17,000 g (4° C.). To each pellet are added 20 ml of water, and the samples are homogenized (Ultra Turrax) for 30 sec. After addition of further 10 ml water the samples are centrifuged for 20 min. at 8500 g (4° C.). Two thirds of the supernatant are discarded, and the light brown upper part of the pellet is whirled up by hand. This supernatant is centrifuged for 30 min. at 37,500 g (4° C.). The pellet is homogenized (Ultra Turrax) for 1 min. in 10 ml of water. The sample is divided into two glasses and a further 25 ml water are added to each (each glass now containes membranes from one brain in 30 ml water). These samples are centrifuged for 30 min. at 37,500 g (4° C.), and the pellets are frozen in acetone/dry ice, corked and stored frozen until use (at least one night).

B. Pretreatment of membranes

On the day of measurements the pellet is frozen in acetone/dry ice for 20 min., and 25 ml of water are added before homogenization (Ultra Turrax) for 1 min. 25 ml of 0.05 N Tris-citrate buffer and 250 μl of 10% Triton X-100 are added, and the sample is incubated for 30 min. at 37° C., and centrifuged at 37,500 g for 20 min. (4° C.). The supernatant is discarded and the pellet is suspended in 0.05 N Tris-citrate buffer (Ultra Turrax, 75 sec.) to a concentration of 30 mg original wet weight/ml. The suspension is placed at room temperature for 20 min. and thereafter kept on ice.

C. Binding assay

Incubation tubes in duplicate receive on ice 780 μl of water, 200 μl of drug dissolved in water, 20 μl of 1 μM $^3$H-GABA (final concentration of $^3$H-GABA in tubes = 10 nM) and 1000 μl of the membrane suspension. After incubation on ice for 5 min., the samples are centrifuged at 31,000 g for 18 min. The supernatant is discarded and the pellet is carefully flushed with 3×5 ml icecold water. Additional water are carefully wiped away with soft paper. One ml of Soluene 350 is added, and the samples are incubated for 30 min. at 37° C. Ten ml of Instagel or Lumagel containing 10 ml of acetic acid per 1 are added, and the radioactivity are determined by liquid scintillation counting. The unspecific binding of $^3$H-GABA is determined by incubating the samples with 1 mM of GABA.

Each series consist of 8 duplicates (1 control, 1 containing 1 mM GABA and one to two series of test compounds in 3 to 6 concentrations).

The means of controls and 1 mM GABA samples are calculated. The measured cpm are plotted against drug concentration on semilogarithmic paper, and the best fitted s-shaped curve drawn. The IC50-values are determined as the concentrations, at which the binding is 50 percent of the total binding minus the unspecific binding.

The results obtained appear from the following table, where the test substances are indicated by the number of the Example describing the preparation of the substance in question.

The corresponding test results for THIP are indicated as references.

TABLE 1

| Test substance | Isoniazide antagonism | Mouse grid shock | $^3$H—GABA binding IC50 |
|---|---|---|---|
| Example 2 | | | $2.0 \cdot 10^{-7}$ |
| Example 3 | weak effect | no effect | $>10^{-4}$ |
| Example 5 | 5.8 | | $1.9 \cdot 10^{-7}$ |
| Example 6 | 1.3 | | $2.7 \cdot 10^{-6}$ |
| Example 7 | 2.1 | | $4.3 \cdot 10^{-7}$ |
| THIP | 1.3 | + | $1.7 \cdot 10^{-7}$ |

The compounds of Formula I and the non-toxic acid addition salts thereof may be administered to animals such as dogs, cats, horses, sheeps or the like, including human being, both orally and parenterally, and may be used for example in the form of tablets, capsules, powders, syrups or in the form of the usual sterile solutions for injection. Results upon administration to human beings have been very gratifying.

Most conveniently the compounds of Formula I are administered orally in unit dosage form such as tablets or capsules, each dosage unit containing a non-toxic acid addition salt of one of the said compounds in an amount of from about 5 to about 100 mg, most preferably, however, from about 10 to 50 mg, calculated as the free amine, the total daily dosage usually ranging from about 20 to about 200 mg. The exact individual dosages as well as daily dosages in particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

When the compound of Formula I is a free amine, preferably R is a higher alkyl group having from 8-17 carbon atoms inclusive, the composition may advantageously be an oily solution for injection, and such solutions often have a very prolonged effect when compared with the corresponding non-acylated compound.

Typical examples of formulas for compositions containing 2-carbamoyl-4,5,6,7-tetrahydroisoxazolo[5,4-c]pyridine-3-one (called Lu 18-028 for short) as the active ingredient are as follows:

1. Tablets containing 10 milligrams of Lu 18-028 calculated as the free base in the form of the oxalate;
   Lu 18-028: 10 mg
   lactose: 37 mg
   potato starch: 74 mg
   gelatine: 2 mg
   talcum: 8 mg
2. Capsules containing per capsule:
   Lu 18-028: 25 mg
   lactose: 40 mg
   magnesium stearate: 0.5 mg Any other pharmaceutical tableting adjuvants may be used provided that they are compatible with the active ingredient, and additional compositions and dosage forms may be similar to those presently used for neuroleptics such as thiothixene, clopenthixol or flupenthixol. Also combination of the compounds of Formula I as well as their non-toxic acid salts with other active ingredients, especially other neuroleptics, thymoleptics, tranquilizers or the like, fall within the scope of the present invention.

As previously stated, when isolating the compounds of Formula I in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates, or bitartrates, embonates and maleates of the amines of Formula I. Other acids are likewise suitable and may be employed if desired. For example; fumaric, benzoic, ascorbic, succinic, salicyclic, bismethylenesalicyclic, propionic, gluconic, malic, malonic, mandelic, cinnamic, cintraconic, stearic, palmitic, itaconic, glycolic, benzenesulphonic, and sulphamic acid may also be employed as acid addition saltforming acids. When it is desired to isolate a compound of the invention in the form of free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals by administering to a living animal body, including human beings, an adequate quantity of a compound of Formula I or a non-toxic acid addition salt thereof. An adequate quantity would be from about 0.5 mg to about 20 mg per kg of body weight per day and from about 20 milligrams to about 200 milligrams per day for oral administration.

It is to be understood that the invention is not limited to the exact details of operation or exact compound or compositions shown and described, as obvious modifications and equivalents will be apparent to one skilled in the art.

We claim:

1. A compound of the formula:

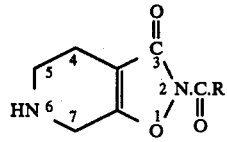

wherein R is an alkyl group, branched or unbranched, having from one to seventeen carbon atoms inclusive, a phenyl group optionally substituted with one or two groups selected from lower alkyl, lower alkyloxy and halogen, a phenylalkyl group, a lower alkyloxy group or a —NHR$^1$ group, wherein R$^1$ is hydrogen, lower alkyl, phenyl or cyclohexyl, as well as pharmaceutically acceptable acid addition salts thereof.

2. A pharmaceutical composition suitable for the alleviation of GABA-system-malfunction-related disorders containing as an active ingredient a compound of formula I as defined in claim 1, or a pharmaceutically acceptable acid addition salt thereof together with a pharmaceutical carrier or excipient.

3. A pharmaceutical composition of claim 2 containing further a minor tranquillizer or a neuroleptic.

4. The method of treating GABA-system malfunction-related diseases in living animals by administering, to the animal, a therapeutically-effective GABA-system-affecting dose of a compound of formula I as defined in claim 1, or a pharmaceutically-acceptable salt thereof.

5. The method of treating pain or myotonic conditions in a living animal by administering, to the animal, a therapeutically-effective analgesic or myotonolytic dose of a compound of formula I as defined in claim 1, or a pharmaceutically-acceptable salt thereof.

6. A compound of claim 1, which is 2-carbamoyl-4,5,6,7-tetrahydroisoxazolo[5,4-c]pyridine-3-one, or a pharmaceutically-acceptable acid addition salt thereof.

7. The composition of claim 2, wherein the compound of formula I is 2-carbamoyl-4,5,6,7-tetrahydroisoxazolo[5,4-c]pyridine-3-one, or a pharmaceutically-acceptable acid addition salt thereof.

8. The method of claim 4, wherein the compound of formula I is 2-carbamoyl-4,5,6,7-tetrahydroisoxazolo[5,4-c]pyridine-3-one, or a pharmaceutically-acceptable acid addition salt thereof.

* * * * *